(12) United States Patent
Harty

(10) Patent No.: US 7,878,995 B2
(45) Date of Patent: Feb. 1, 2011

(54) INTEGRAL HEAD, NECK, AND UPPER TORSO IMMOBILIZER

(76) Inventor: Robert D. Harty, 500 Heartland, New Lenox, IL (US) 60451

( * ) Notice: Subject to any disclaimer, the term of this patent is extended or adjusted under 35 U.S.C. 154(b) by 2035 days.

(21) Appl. No.: 10/633,450

(22) Filed: Jul. 31, 2003

(65) Prior Publication Data

US 2005/0027222 A1 Feb. 3, 2005

(51) Int. Cl.
*A61F 5/00* (2006.01)

(52) U.S. Cl. .......................................... 602/18; 128/845

(58) Field of Classification Search .................. 602/19, 602/17, 18; 128/DIG. 23, 845, 870
See application file for complete search history.

(56) References Cited

U.S. PATENT DOCUMENTS

| | | | | |
|---|---|---|---|---|
| 3,220,406 A | * | 11/1965 | Connelly | 602/18 |
| 5,054,475 A | * | 10/1991 | Calabrese et al. | 602/17 |
| 5,205,813 A | * | 4/1993 | Schmidt | 602/17 |
| 5,334,133 A | * | 8/1994 | Carroll | 602/18 |
| 6,045,523 A | * | 4/2000 | Donaldson | 602/18 |
| 6,966,321 B2 | * | 11/2005 | Hess | 128/870 |

* cited by examiner

*Primary Examiner*—Kim M Lewis
(74) *Attorney, Agent, or Firm*—Cherskov & Flaynik

(57) ABSTRACT

A device to simultaneously immobilize the head, neck and upper torso of a patient, the device comprising a first substrate for supporting the back of the patient's head, a second substrate in communication with the first substrate, whereby the second substrate is adapted to encircle the patient's neck; and a third substrate in communication with the second substrate, whereby the third substrate contacts the patient's chest.

14 Claims, 10 Drawing Sheets

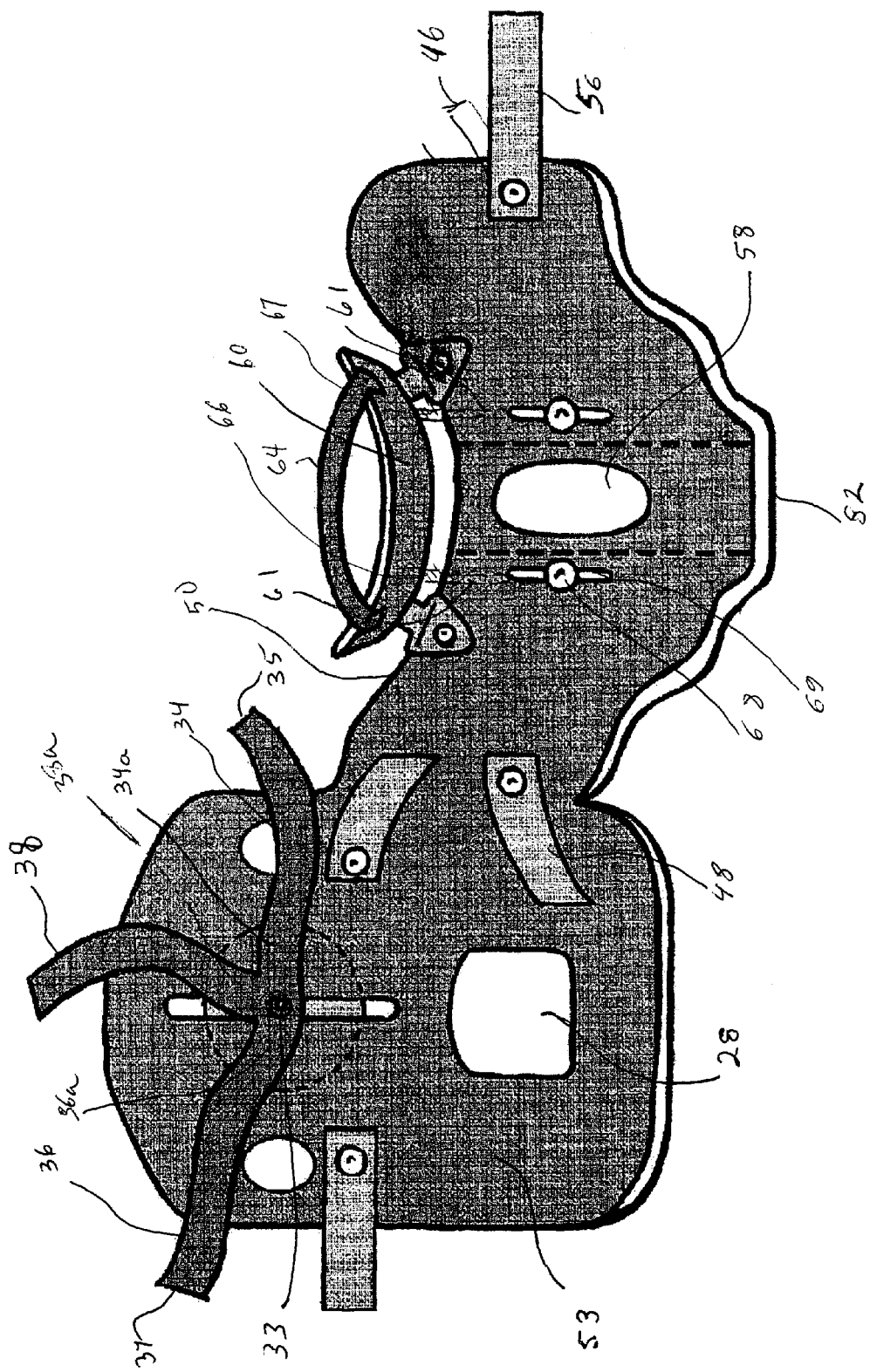

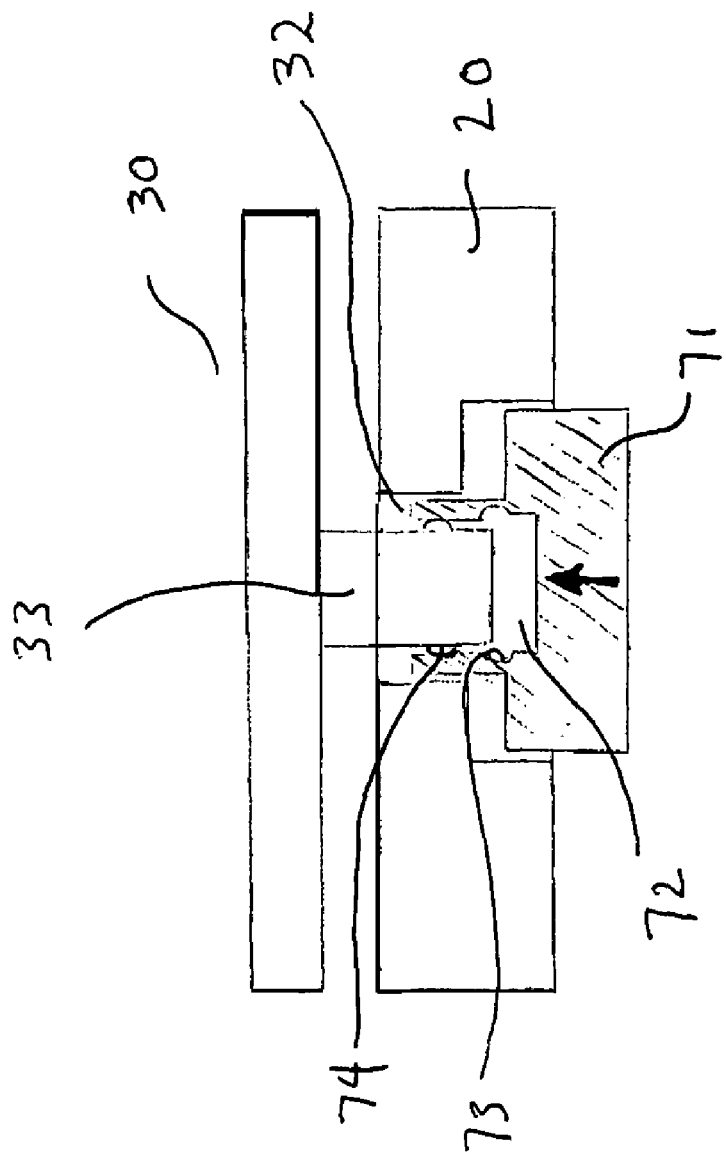

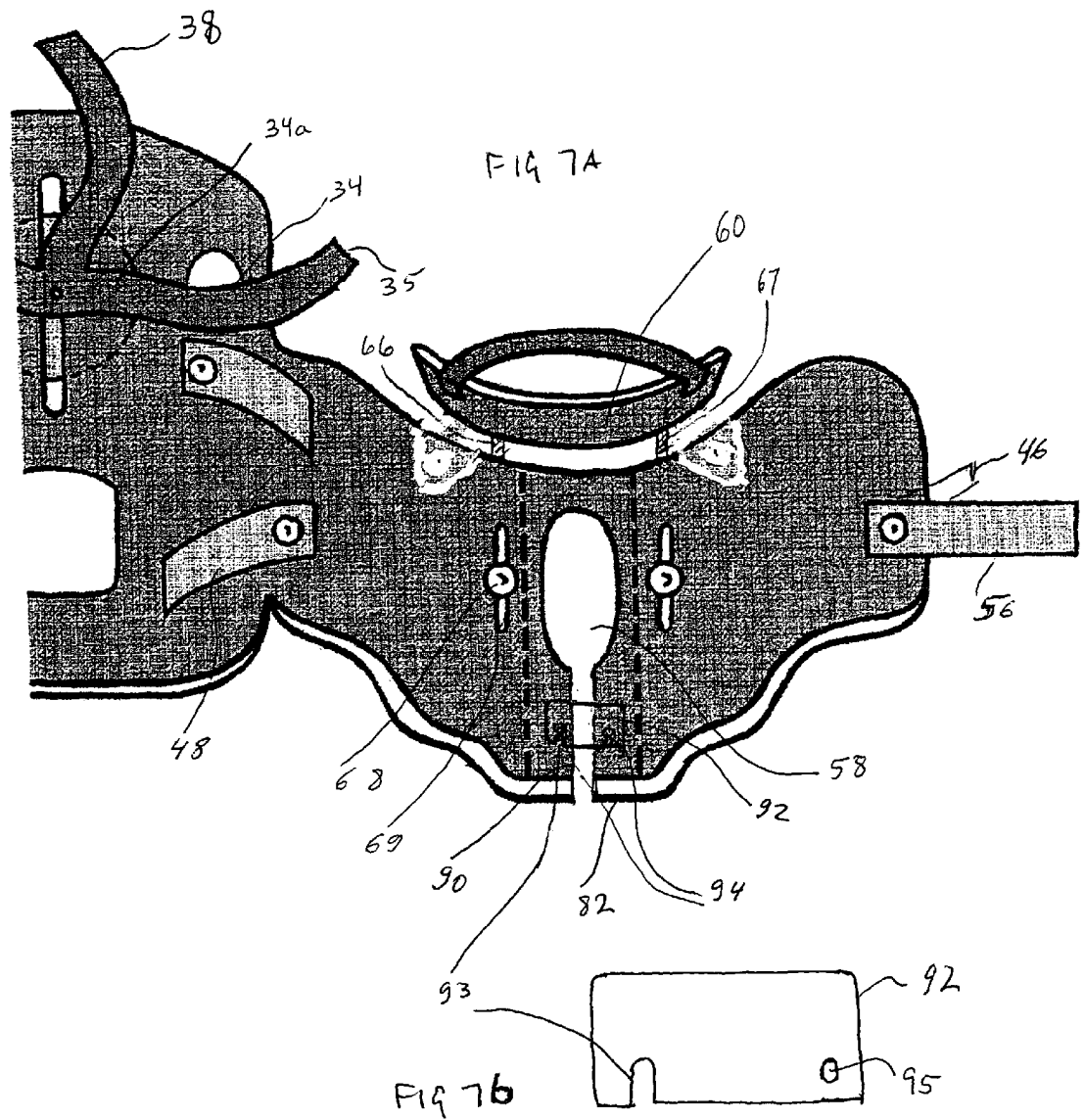

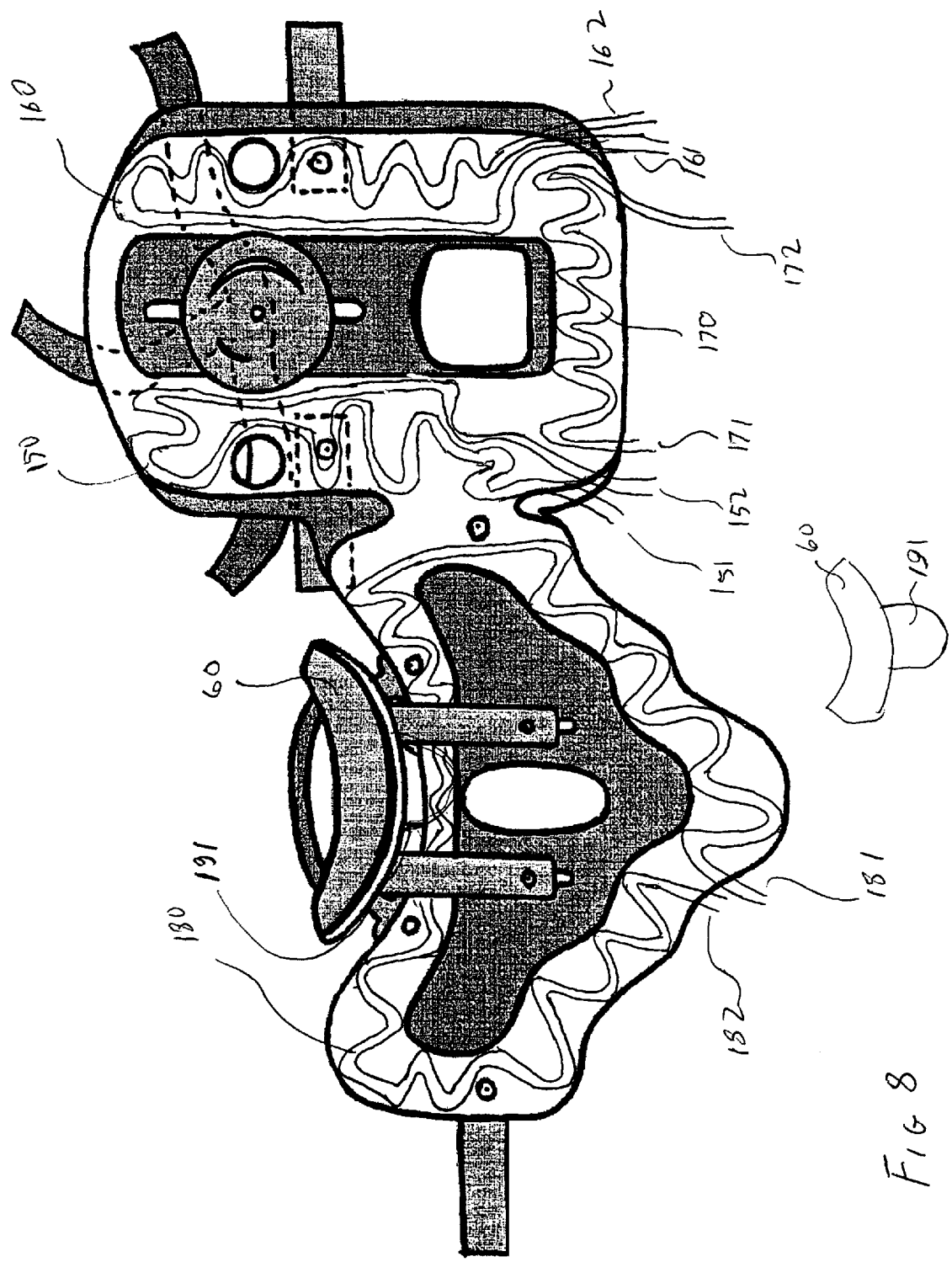

INTEGRAL HEAD, NECK, AND UPPER TORSO IMMOBILIZER

BACKGROUND OF THE INVENTION

1. Field of the Invention

The present invention relates to the field of patient immobilizers and, more particularly, to devices that restrain and support a patient's head, neck, and upper torso during emergency treatment and transportation and during short- and long-term rehabilitation.

2. Description of the Prior art

The human head is very vulnerable to injuries at the back of the head and particularly at the base of the skull where the skull provides little or no protection. This is a most critical area for it is there that the spinal cord emerges from the brain. Injury to the spinal cord threatens every aspect of human physiology: control of respiration, heart rate, body temperature, consciousness, swallowing, vaso-constriction and dilation, and a myriad other autonomic nervous system functions. Injury to the brain stem or spinal cord may result in paralysis and even death.

The base of the human head and neck are frequently injured in a variety of situations. Also, the head, neck, and upper shoulders closely interact with each other. For instance, motion of the head or the shoulders may seriously aggravate a pre-existing neck injury. At the place of injury; it is imperative that the patient be immobilized for subsequent transport and short-term or long-term treatment. Predominantly, the present practice is to provide the patient with a cervical collar. Typical cervical collar designs have many disadvantages: they fail to immobilize the head and they also apply excessive pressure in the brain stem area, a most dangerous circumstance if a fracture in that area had occurred and swelling ensued. In such an instance, the cervical collar could aggravate the fracture and aggravate brain damage or spinal cord damage.

There are several head and neck supports already available. Many of these are intended to support the head and or the neck while the patient is walking (U.S. Pat. No. 5,201,702). Others are intended to immobilize the head alone (U.S. Pat. No. 5,211,185) or the neck alone (e.g. U.S. Pat. 4,677,969).

A need exists in the art for a device to isolate a brain stem or spinal cord injury from all surrounding anatomical structures. Such a device would immobilize a patient's head, neck, and upper body relative to each other and maintain these immobile with respect to a backboard, particularly preventing lateral movement (i.e., left to right). Such a device also would provide access to the trachea, brain stem, cervical spine, ears, face and other areas so as to facilitate observation and treatment of these areas during immobilization and transport.

SUMMARY OF THE INVENTION

It is an object of the present invention to provide a device for immobilizing the head, neck, and upper torso of an emergency patient or one under short-term or long-term treatment that overcomes many of the disadvantages of the prior art.

It is a further object of the present invention to provide a device for immobilizing the head, neck, and upper torso of an emergency patient that may be utilized with different sized patients. It is a feature of the present invention that it includes several adjustable components. An advantage of the present invention is that it ensures that an emergency team equipped with the present invention will be able to treat most likely casualties.

Another object of the present invention is to provide a device for immobilizing the head, neck, and upper torso of an emergency patient that allows treatment of the patient's trachea or cervix while the patient is supported by the device. It is a feature of the present invention that it includes openings to facilitate simultaneous access to the trachea and the cervix. An advantage of the present invention is that it allows for an emergency tracheotomy, treatment of the lower skull (such as the base of the skull and/or the brain stem), or treatment of the cervical spine while the patient is wearing the device.

Yet another object of the present invention is to provide a device for immobilizing the head, neck, and upper torso of an emergency patient that does not impede blood flow while the patient is wearing the device. A feature of the present invention is that it includes patient restraint points at a multitude of locations thus distributing the force exerted by the device. An advantage of the present invention is that it eliminates the danger of excessive contact pressure occurring at one or more locations while the patient is wearing the device.

Still another object of the present invention is to provide a device for immobilizing the head, neck, and upper torso of an emergency patient that provides adequate support to the occipital region while the patient is supported by the device. It is a feature of the present invention that it includes an adjustable occipital cushion. An advantage of the present invention is that-it allows occipital support for different sized patients and is thus adjustable so as to be used by different sized patients.

Yet another object of the present invention is to provide a device for rapidly immobilizing the head, neck, and upper torso of an emergency patient with respect to a backboard. It is a feature of the present invention that it includes a plurality of tethers that may be slid into pre-existing grooves fixed with respect to a backboard. An advantage of the present invention is that it allows immobilization with respect to the backboard by means of a few rapid sliding motions.

Briefly, the invention provides a device to immobilize the head, neck and upper torso of a patient, the device comprising a first substrate for supporting the back of the patient's head; a second substrate in communication with the first substrate, whereby the second substrate is adapted to encircle-the patient's neck; and a third substrate in communication with the second substrate, whereby the third substrate contacts the patient's chest. The invention provides access to the trachea, ears, facial area, brain stem and cervical spine while also eliminating lateral movement and neck and chin dropping of the patient.

BRIEF DESCRIPTION OF THE DRAWINGS

The foregoing invention and its advantages may be readily appreciated from the following detailed description of the invention, when read in conjunction with the accompanying drawings in which:

FIG. 5 is a plan view of the outer surface of an integral head, neck, and upper torso restraint in an opened position, in accordance with features of the present invention;

FIG. 6 is a cross-sectional view detailing attachment of an occipital cushion in the invented device, in accordance with features of the present invention;

FIG. 7a is a plan view of the outer surface of an alternate embodiment of a sternum plate of an integral head, neck, and upper torso restraint, in accordance with features of the present invention;

FIG. 7b is a plan view of a means to close an access channel on the breast plate of the invented device, in accordance with features of the present invention;

FIG. 8 is a plan view of a fluid circulation arrangement for the inner surface of an alternate embodiment of an integral head, neck, and upper torso restraint, in accordance with features of the present invention;

DETAILED DESCRIPTION OF THE INVENTION

Figure 1:
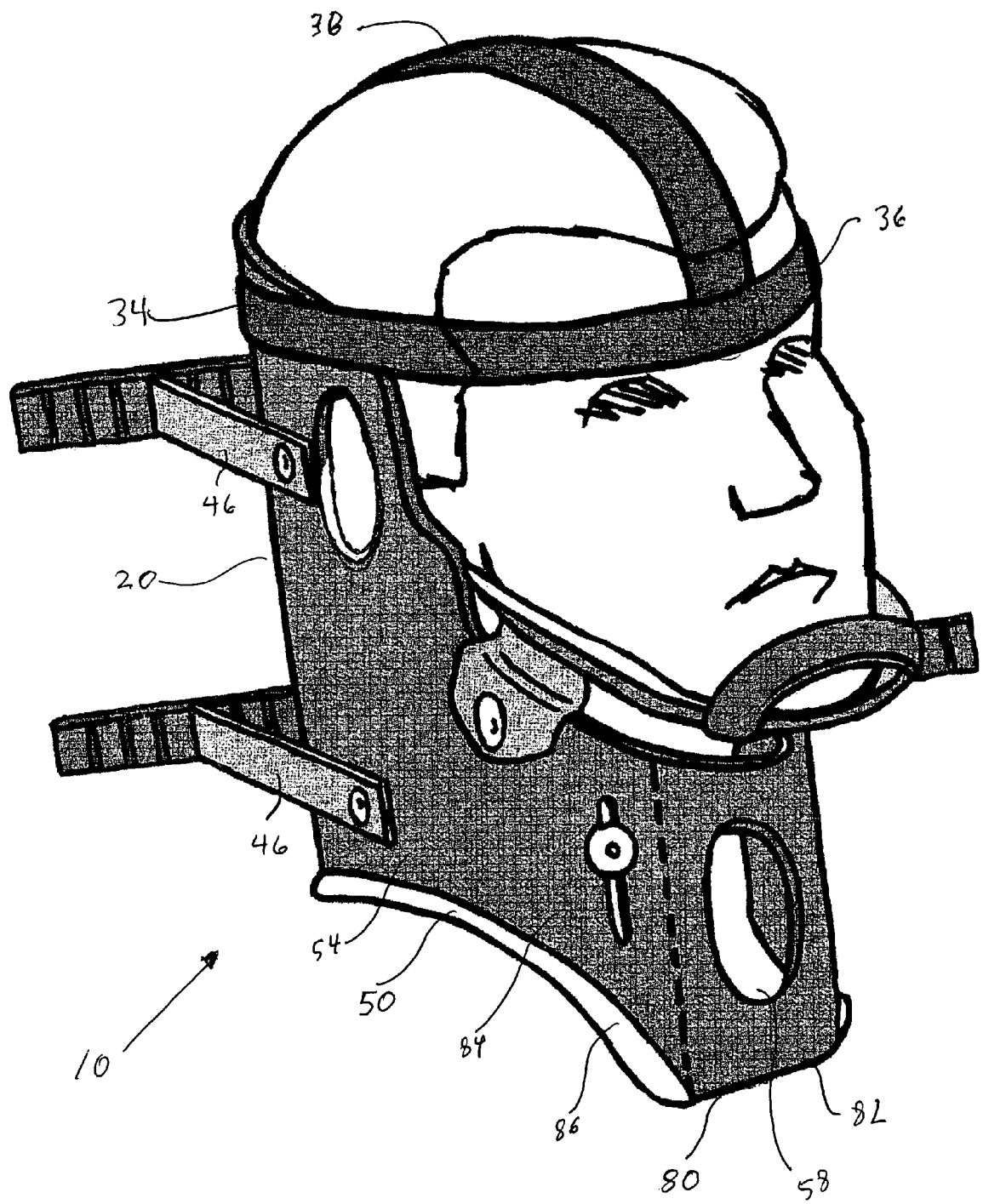
FIG. 1 is a front perspective view of an integral head, neck, and upper torso restraint in use, in accordance with features of the present invention.

The present invention provides an integral head, neck, and upper torso restraint to immobilize a patient with respect to a backboard. As shown in FIG. 1, the restraint, generally designated as 10 is comprised of three components: a back-of-the-head support 20, a neck support 50, and a sternum plate 80. While the device is illustrated with the three components integrally molded with each other, the components can be removably attached and juxtaposed to each other.

Each of the three components comprises an outer shell and a soft inner lining. Compared to materials comprising the outer shell, the inner lining materials are relatively pliable. A variety of materials may be used for the outer shell, and similarly for the lining. However distinct advantages accrue when both the outer shell and the inner lining consist of transparent materials. This allows visual inspection of the head, neck, and shoulders while the patient remains restrained. Transparent substrate also allows for the quick detection of hemorrhaging or other injury. Also, the entire device is radio-translucent and x-ray transparent and this confers the additional advantage of affording immobilization during noninvasive diagnosis.

Occipital Region

Support Detail

Figures 2A, 2B:
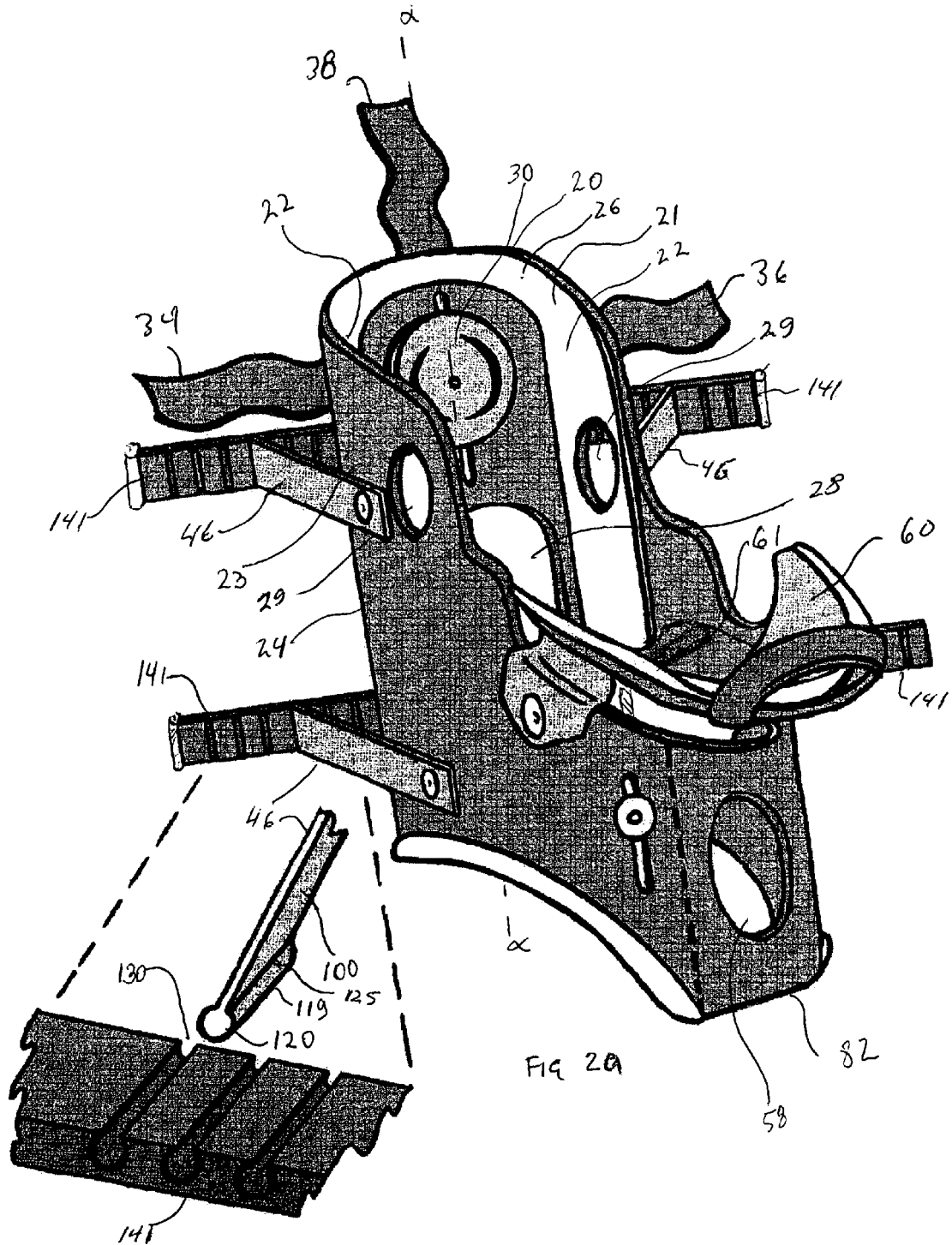
FIG. 2*a* is a front perspective view of an integral head, neck, and upper torso restraint when not in use, in accordance with features of the present invention.
FIG. 2*b* is a detailed view of a means for securing to a backboard an integral head, neck, and upper torso restraint, in accordance with features of the present invention.

Referring to FIG. 2a an internal surface 21 (i.e., a patient-contacting surface) of the head support 20 of the device defines an arcuate-shaped surface adapted to support a patient's cervical region. The device is configured so that while it is worn, the support extends longitudinally upwardly from between the patient's shoulders at approximately the first thoracic vertebrae to approximately the top of his/her cranium. The fact that the head support extends to the top of the cranium alleviates the pressure on any portion of the head. Lateral to the longitudinal axis (designated as a) of the support, the surface 21 curves inwardly to form a pair of opposing concave surfaces 22. The concave surfaces 22 are adapted to envelop at least part of the temporal region of the cranium, particularly around the ears. The head support 20 comprises ear openings 29. Typically these would be oval shaped (as depicted in FIG. 1), with exemplary dimensions being approximately two inches long and one inch wide. Alternatively, the ear openings could be more circular.

An external surface 23 of the head support comprises a substantially rigid outer shell 24 which is lined with an inner cushioning material 26 such as rubber foam, gel, or an inflatable cushion. This inflatable cushion can further define an inflatable bladder or series of bladders adapted to receive fluid of various temperatures and phases. It is this cushioning material which lines the internal surface 21.

Figure 4:
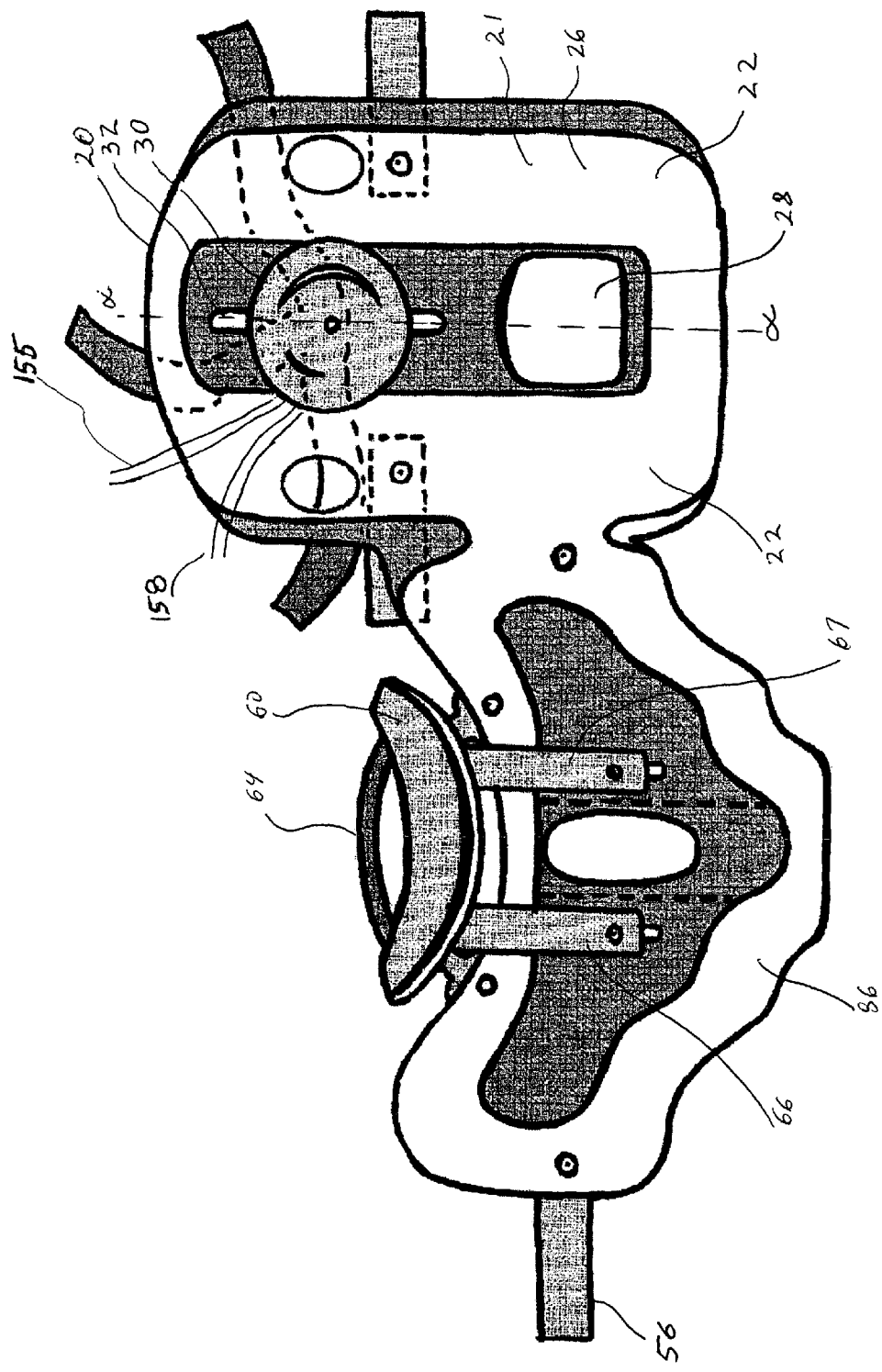
FIG. 4 is a plan view of the inner surface of an integral head, neck, and upper torso restraint in an opened position, in accordance with features of the present invention.

FIG. 4 is a planar view of the internal surface surface (i.e. the surface contacting the patient) of the present invention in an open configuration. The back of the head support defines an opening 28 through which the cervical region may be observed and treated. This opening 28 ensures that no pressure is applied to the brain stem while a patient is wearing the device.

The lining of the internal surface 21 may comprise a plurality of reversibly deformable substrates, such as conduits, which may receive any suitable fluid such as air (for cushioning), a heated fluid, a cooled fluid, or a combination of such fluid phases and temperatures. The embodiment depicted in FIG. 8 comprises three conduits, such as tubes 150, 160, and 170, for the right, left, and bottom sides respectively of the head support 20. The conduits are in contact with the patient-surface and reversibly held in place via a series of hook and pile loops (the later of which are attached to the internal surface), or else contacting underlying portions of the internal surface defining channels adapted to frictionally receive the tubes. The tubes also can be irreversibly attached to the internal surface via adhesive. Lastly, the fluid conduits can be integrally molded with the internal surface.

The fluid conduits each have an inlet 151, 161, and 171, respectively, and an outlet 152, 162, 172, the outlets facilitating the filling and evacuation of the tubes.

Fluid ingress and egress to and from the tubes is regulated via valve means attached directly to the inlet and/or outlet ports, or attached remotely to fluid supply entities and/or spent fluid reservoir entities (not shown). The invented configuration accommodates the existence of valves at both the ends of the inlet and outlet ports and also at the fluid supply entities and spent-fluid reservoir entities.

The three-tubes configuration allows the application of different fluids to different areas of the head if necessary. If not, one may join two or three tubes in series or in parallel. Other tubing arrangements can be used as well.

As illustrated in. FIG. 4, the back of the head support further comprises an occipital cushion 30 slidably received in a channel 32 extending along the longitudinal axis α of the back of the head support 20. The cushion 30 is typically 3 to 4 inches in diameter. Preferably, the surface of the cushion opposing the patient's head is concave, thus allowing the head to rest comfortably on the cushion. The cushion 30 may utilize the same materials as those listed supra in conjunction with the inside surface 21 of the head support. One may provide means to inflate the cushion as well. The channel 32 extends completely through the support in a transverse manner.

FIG. 6 illustrates an exemplary occipital cushion-fastening configuration, comprising the cushion pad 30, the pad mounting post 33, and a cushion pad fastening unit 71 adapted to slidably receive and frictionally engage the post 33. Shown in an unengaged configuration, the cushion is locked in place along the channel 32 defined by the back substrate 20 of the collar when the fastening unit 71 is actuated in the direction of the arrow, that is when the fastening unit is slid radially inwardly and approximately in a direction 90 degrees from the longitudinal axis of the collar. This sliding (and therefore cushion locking) action can be effected manually by emergency personnel at the scene, or by the weight of the patient's head against the backboard.

The fastening unit defines a cavity 72 the sides of which define an annular grove 73 adapted to receive a protuberance extending about the periphery of the mounting post 33.

The slidable-cushion feature equalizes the pressure exerted on the patient's head while minimizing head motion. The cushion may comprise rubber foam, a gel, or inflatable material, inter alia. As shown in FIG. 4, the cushion may be provided with an inlet tube 155 and an exhaust tube to 158 to effect such inflation. The inflating fluid may be air, water, or any other suitable fluid.

Also, there are many other means for securing the cushion 30 in place, including a male-female configuration whereby the cushion post 33 receives a nut, with the collar substrate 20 intermediate therebetween.

Patient and Backboard

Fastener Detail

Figure 3:
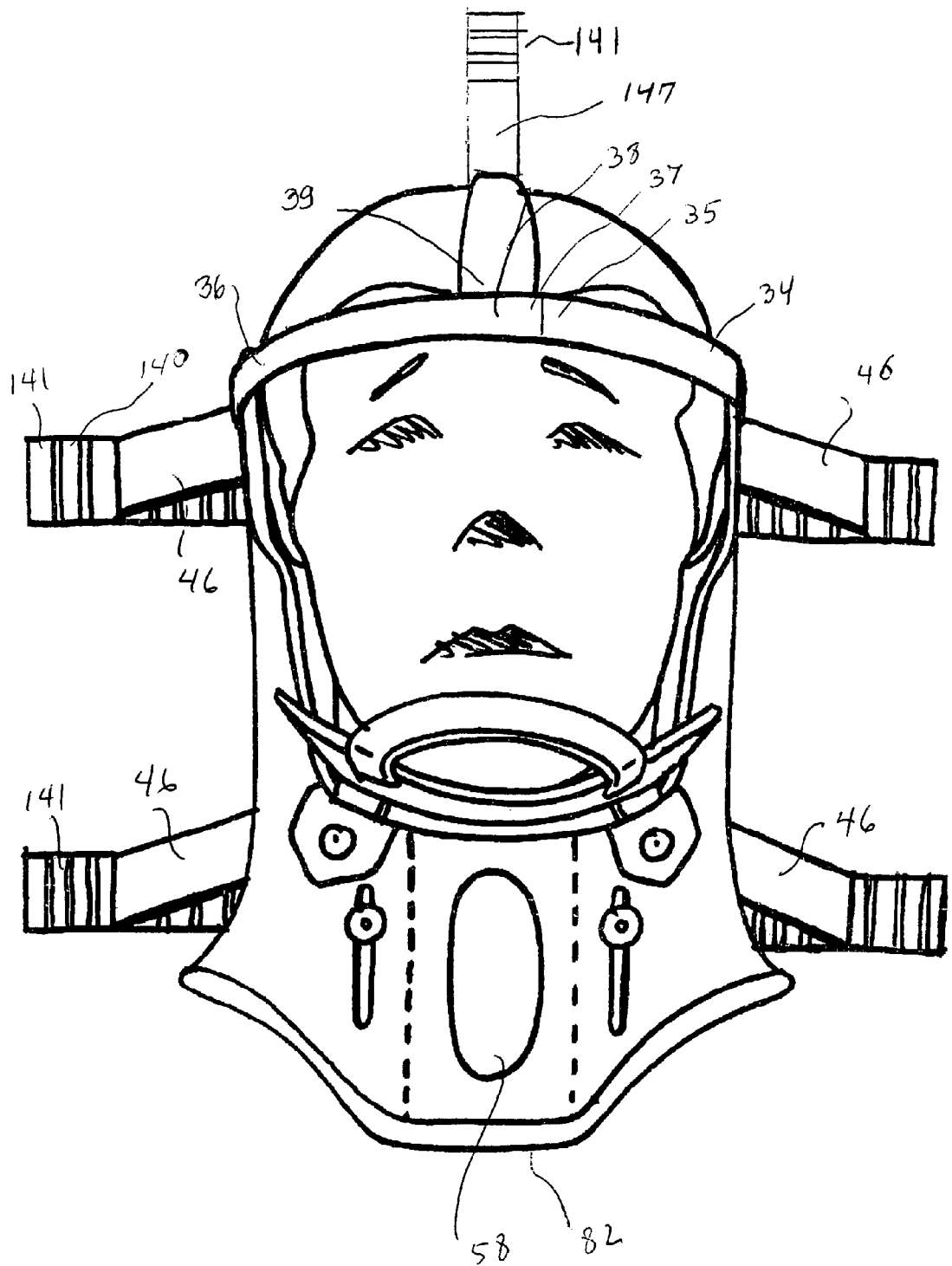
FIG. 3 is a front view of an integral head, neck, and upper torso restraint in use, in accordance with features of the present invention.

Once a patient is fitted into the device, a means for immobilizing the top of the patient's head relative to the device is utilized. A possible attachment means is a suction cup attached to the back 20 of the head support thus allowing rapid immobilization of the invented device with respect to the backboard. One device immobilization means is illustrated in FIG. 3 and comprises a plurality of straps 34, 36, 38 the first ends of which are attached to the head support or the cushion. The second ends of the straps 35, 37, 39 are configured to be removably connected to each other. As such, these second ends are terminated with snap fit arrangements, ties, hook-and-pile configurations, or similar reversible attachment means.

FIG. 5 illustrates a preferred embodiment where two straps 34, 36 extend laterally (and somewhat perpendicular from the longitudinal axis α) from the axis α, a first end of each of the straps originating from the occipital cushion 30 that is in sliding communication with the head support 20. Optimally, the straps 34 and 36 extend from the support 20 so as to run slightly above the patient's ears. Another strap 38 extends upwardly from, and somewhat coaxially to, the longitudinal line a of the support.

Straps 34, 36, and 38 that envelop the top of the head are secured either to the support shell 20 or to the post 33 that supports the cushion 30. The latter connection configuration allows the straps to provide optimal support for the head. A myriad of attachment means of the first ends of the straps 34, 36, and 38 to the bolt 33 are suitable. Alternatively, the straps 34 are the embodiment of the first and seconds ends of a single strap, whereby the single strap matingly communicates with a region of the exterior surface 23 of the head support 20. Such mating communication includes, but is not limited to, a snap fit arrangement, hook-and-pile configurations, or a plurality of slits, situated parallel to the longitudinal axis of the head support and adapted to slidably receive the strap 34. FIG. 5 depicts the first ends 34a, 36a, and 38a of the straps 34, 36, and 38 attached to the bolt 33.

In use, the straps 34, 36 envelop the patient's head and meet at the patient's forehead where the second ends 35, 37 are joined to each other to form a head band. The third or "top" strap 38 is joined to the head band after extending along the hemisphere line (i.e., from back to front) of the patient's head. As noted supra, these junctions may be effected by hook-and-pile fastening means, belt and buckle arrangements, or by other similar fastening means.

Any flexible substrate is a suitable strap constituent. As such, exemplary materials include, but are not limited to, plastic, cloth, nylon, rubber, and leather. The patient's comfort is enhanced if the straps consist of or are lined with a soft material such as rubber foam or sponge (not shown).

The invented immobilization collar also provides a means for attaching the device to the backboard. These attachment means immobilize the collar to the backboard on which the patient rests during transport. One such attachment means is a suction cup or plurality of suction cups integrally molded with an outer surface of the neck support substrate 20. A suitable location for such a suction cup is at the post 33 attached to the occipital cushion, so that the back of the suction cup is fastened to the post 33.

Another attachment means is illustrated in FIG. 2a. From the top, left, and right sides of the exterior surface 23 of the head support 20 extend a plurality of flexible backboard tethers. FIG. 2a depicts two pairs of backboard tethers 46 extending laterally from the head support 20 and generally radially from the longitudinal axis α of the head support as well as another tether 147 extending along the axis α. Usually all the tethers would be used but there may be circumstances where only the top tether 147, or only one pair of lateral tethers would be used.

As shown in the detail in FIG. 2b, each tether comprises a substrate 100 such as a webbing, strip, or other elongate substrate having a first end attached to the head support 20. The second end terminates in a bead 119 having a cross-section 120 wider than the thickness of the elongate substrate. The bead is designed so that it may be slid into a matching groove 130 or cleat that has been milled or otherwise integrally molded with the backboard. Preferably, the webbing is rigid to facilitate complete immobilization of the collar to the backboard.

In the alternative, substrates 141 defining the female portion of the tether fastening means, are provided whereupon such grooves 130 have been molded. These substrates in turn are adapted to be fastened to a backboard (not shown). As shown in FIG. 2b, the cleat groove cross-section snugly fits that of the bead 120 at the bead's point of contact 125 with the membrane 100 so as to retain the bead in the cleat. While FIG. 2 illustrates beads with circular cross-sections, square, triangular, and other cross-sections also are possible.

The cleat strips 141 may be fastened to the backboard by VELCRO, glue, screws, adhesive, and a myriad of other means. Such fastening can be reversible, or irreversible. The irreversible attachment of the strips to backboards is appropriate in short backboard situations, inasmuch as c-collars typically are always used therewith. Possible embodiments include where the cleat strips are integrally molded to the backboard or where the female aperture portions of the fastening means are milled or otherwise cut into the surface of the backboard. Another possible embodiment comprises a panel into which grooves to receive the beads terminating the attachment strips have been cut therethrough and where said panel is matingly and removably attached to the backboard.

Alternatively, instead, or in conjunction with the tether 46 and female mating surface 141, double backed tape or fastening means is used to reversibly anchor a dorsal surface 53 of the collar (i.e., the backboard-contacting surface) to the backboard.

Neck Support Detail

A salient feature of the device is its ability to simultaneously support and immobilize a patient's head, neck and upper chest.

As shown in FIG.1, the neck support region 50 is continuous with the back of the head support 20 and radially extends from the longitudinal axis α of the head support. Preferably, the neck support region 50 is integrally molded with the head support 20.

The neck support region 50 comprises a substantially rigid outer shell 54 that is lined with an inner cushioning 52 material such as rubber foam, gel, or an inflatable cushion. While the shell 54 of the neck support is preferably continuous with the outer shell 24 of the back of the head support 20, the inner cushioning material 52 may be distinct and separate. As shown in FIG. 8, the inner cushioning material 52 may comprise a tube 180 with inlet 181 and outlet 182 to allow inflation of this cushioning material similar to that described supra for the head support 20. Ideally, the neck support 50 extends around the patient's neck. In such an instance, the outer shell 54 is either be hinged or consist of a material that is flexible enough to wrap around the neck and accommodate for swelling while still offering rigidity. Once wrapped around the patient's neck, the neck support may be closed by a variety of means. A hook-and-pile closure (e.g., a Velcro®-type fastener) 56 (See FIG. 7a) is commonly used for such purposes and it is appropriate here in that it allows an adjustable fit around the neck. An alternative embodiment comprises a removable neck support attached to the head support by means of a hinge with a removable hinge pin (not shown). Then, the neck support may be detached by removing the hinge pin.

As shown in FIG. 7a, the neck support region 50 has a forwardly facing region defining an aperture 58. This aperture 58 provides access to the front of the neck so as to facilitate the performance of a tracheotomy, or to control carotid blood flow, if necessary.

Superior to the aperture is a region of the neck support region adapted to receive a chin cup 60. (See FIG. 5). The chin cup, directed upwardly, is optionally hingeably attached to the neck support 50 so as to allow limited jaw movement while the patient is immobilized by the device. Alternatively, the chin cup is attached to the neck support 50 via a plurality of downwardly depending adjustment posts 66, 67 in frictional engagement with apertures 61 defined by an upwardly facing surface of the neck support.

Several other means exist to attach the adjustment posts 66, 67 to the neck support 50. One such method is depicted in FIG. 5, where a thumb screw 68 (actuated from the exterior surface of the neck support) penetrates through the neck support by means of a transverse channel 69 to be threadably received by the post 66, 67, or else to frictionally secure the post to the inside surfaces of the apertures 61. Sliding the screw 68 along the channel 69 allows one to adjust the height of the chin cup 60. The patient's chin is secured to the chin cup 60 by a chin strap 64.

Figure 9A:
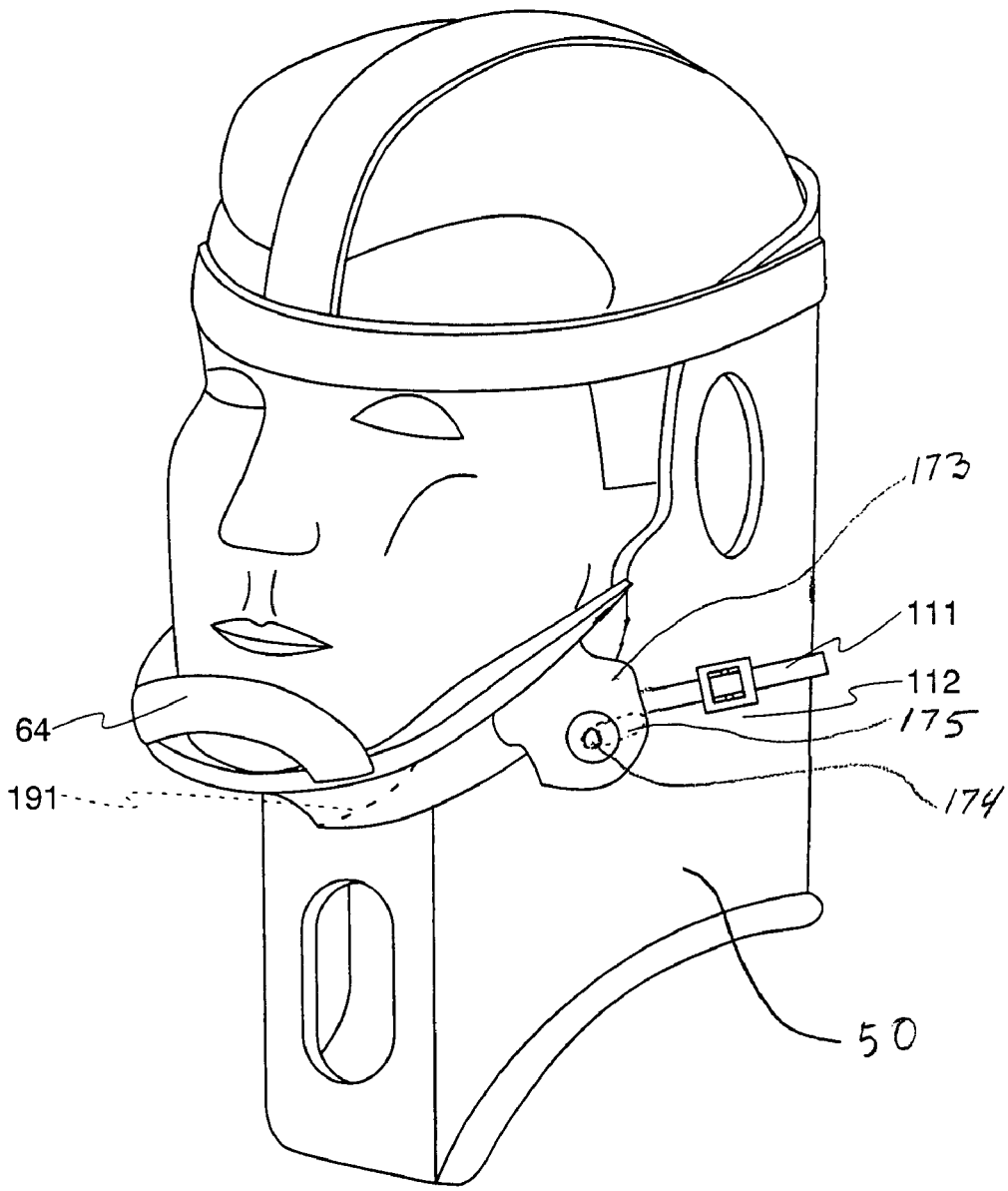
FIG. 9a is a plan view of the outer surface of an alternate embodiment of a chin cup adjustment device for an integral head, neck, and upper torso restraint in accordance with features of the present invention.

An additional chin cup adjustment is illustrated in FIG. 9a. This embodiment allows radial movement of the chin cup 60 (and therefore, of the patient's chin) relative to the collar. This configuration prevents a patient's chin from slipping behind the chin cup, which is often the case in "no neck" situations where a patient has a double chin preventing seating of a typical chin cup firmly against the lower jaw line of the patient. Specifically, the chin cup adjusting feature in FIG. 9a allows adjustment of the cup in a direction perpendicular to the device axis α. The chin cup 60 comprises on either side a depending lateral tab 173 to which is attached a transversely extending pivot member 174. The pivot member 74 is adapted to be received in a slot 175 formed on either side of the neck support 50.

Figure 9B:
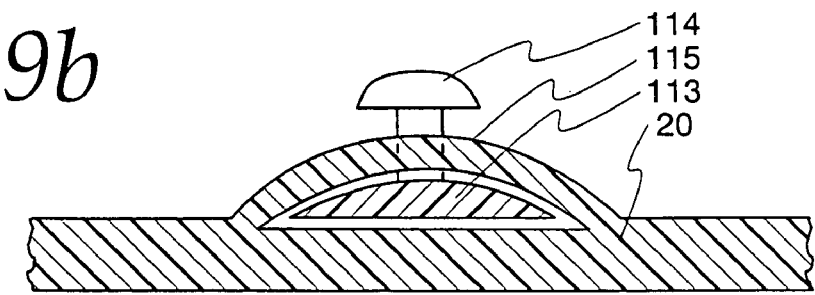
FIG. 9b is a detailed view of the outer surface of an alternate embodiment of a chin cup adjustment device for an integral head, neck, and upper torso restraint in accordance with features of the present invention.

The chin cup 60 also comprises lateral rods or straps 111 on either side of the chin cup. In FIG. 9a the strap 111 passes through a buckle 112 affixed to the back support 20 and one adjusts the chin cup 60 by pulling on the strap 111. The strap/buckle configuration can be replaced by a hook-and-pile configuration (e.g. VELCRO®) or as depicted in FIG. 9b, the strap 111 can be replaced with a rigid or semi-rigid substrate 113 and the buckle 112 replaced with a screw/threaded-aperture configuration.

Figure 9C:
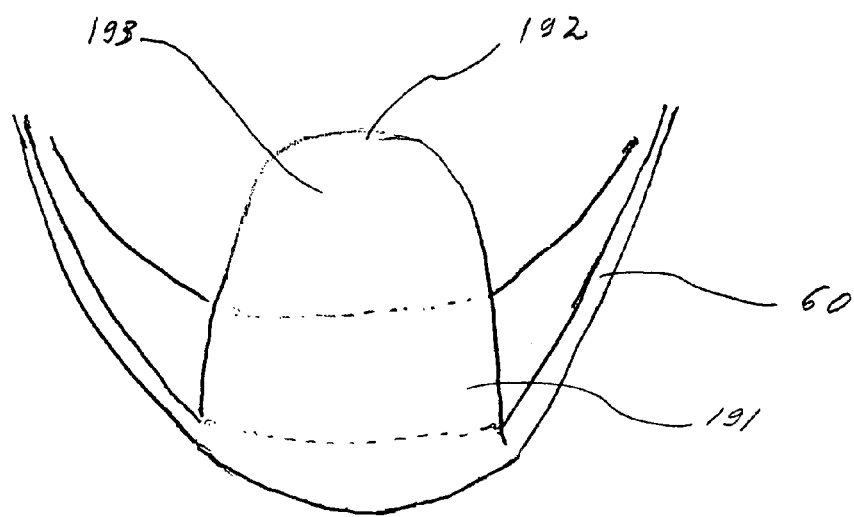
FIG. 9c is a detailed view of the outer surface of an alternate embodiment of a chin cup device for an integral head, neck, and upper torso restraint in accordance with features of the present invention.

To further ensure that a patient's chin does not slip off the chin cup 60, an alternative cup configuration is depicted in FIG. 9c which shows the chin cup 60 as seen from above. As shown in FIG. 9c, the cup defines an inwardly extending cushioning substrate 191 (see also FIG. 8 and dotted line in FIG. 9a), the later to come in contact with the double chin of the "no neck" patient. The inwardly extending substrate 191, which can be reversibly deformed is integrally molded with the cup and resembles a tongue. An inwardly directed tip 192 of the tongue or substrate stops at a point directly opposing the area of the patient's neck which corresponds to the location of the trachea or "adams apple". An upwardly directed surface 193 of the tongue is adapted to contact the double chin of the patient.

These adjustment features allow EMS personnel to adapt just one device to accommodate children or adults having a wide range of neck heights. Especially, the presence of this adjustment allows the use of a narrower collar than usually required, thus enabling the use of the device with individuals with very short necks.

Sternum Plate Detail

Another salient feature of the device is the sternum plate. The plate serves as a means for providing additional rigidity and support to the device's structures, situated superior to the sternum plate.

Most cervical collars terminate flush with the clavicle. Alternatively, some collars may have a short and downwardly extending projection that sometimes contacts the patient's pre-sternal notch, causing much pain thereby. Generally, typical cervical collars provide inadequate head immobilization in that they fail to prevent the patient from nodding his or her head down.

As shown in FIG. 1, the present invention comprises a sternum plate 80 that extends down to the second or third rib. The plate 80 is continuous with the neck support 50. The sternum plate has a gently curved lower border 82 adapted to rest comfortably on the patient's chest. Yet, by virtue of its lower border extending some distance down the patient's chest, it prevents the patient from nodding his or her head.

The plate 80 comprises a substantially rigid outer shell 84 that is lined with an inner cushioning material 86 such as rubber foam, gel, or an inflatable cushion. While the shell 84 must be continuous (and perhaps integrally molded) with the shell 54 of the neck support 50, the inner cushioning material 86 may be distinct and separate.

FIG. 7a depicts an alternate embodiment of a sternum plate. It comprises a channel 90 leading to the trachea aperture 58. This channel allows using the invented device with a patient who already has undergone a tracheotomy and who has been fitted with a tracheal tube so that the patient is fitted with the device while the tracheal tube remains embedded in the trachea. The channel 90 has a reversible closure. The channel 90 is reversibly bridged by a plate 92 that may hingeably swing about an aperture 95 and slide into place along slit 93, to be anchored to the sternum plate by means of screws 94 (See FIG. 7b). Alternatively, the channel may be bridged by a strap attached to the sternum plate via a hook-and-pile arrangement-or other reversible attachment means. Additionally the strap-comprises a rigid substrate to confer rigidity across the tracheal tube access channel 90.

Inflatable Lining

For the Immobilizer.

An alternative embodiment of the present invention is illustrated in FIG. 8. It comprises a plurality of reversibly deformable membranes, illustrated as conduits, embedded in the inner lining of the device. Specifically, FIG. 8 depicts four separate regions 201, 202, 203, and 204 each of which may be filled separately by a fluid, either a liquid or a gas. Each conduit has an inlet 210 and an outlet 212. One may vary the nature of the fluid, its temperature, and its pressure for each of the four regions, depending on the clinical needs, without affecting other parts of the head, neck, and upper torso.

The three components of the device operate in cooperation in several ways. There is structural cooperation between the elements that gives the device the required rigidity while allowing great flexibility. There are two openings allowing access to the trachea 58 and to the occipital vertebrae 28. These do not compromise the rigidity of the device or its resistance to torsion because these openings are flanked by the sternum plate 80 and the back of the head support 20 respectively.

Particularly with regard to the trachea opening, and as is illustrated in FIG. 7a, the device is configured so as to allow medical personnel to fit the device to a patient who is already connected to some other medical equipment (such as a suction device) via a tracheotomy or intravenous lines to neck blood vessels. The already established interaction with the medical equipment need not be interrupted during fitting of the device with the patient, inasmuch as a periphery 90 of the trachea aperture is adapted to slidably accommodate a trachea tube or intravenous lines for ultimate nesting within the confines of the trachea aperture. Rigidity of the neck substrate at the trachea aperture is assured via a swing plate 92 before and after passage of the subject lines through the aperture periphery (See FIG. 7b). The swing plate is hingeably attached to the neck substrate a single point 95 with any standard attachment means.

There is functional cooperation between the components of the device in that there are several adjustable features that allow the device to be used with differently sized individuals:

the head straps 34, 36, 38 have adjustable closures so as to accommodate a wide range of head sizes;
the position of the occipital cushion 30 is adjustable along the channel 32 and therefore along the longitudinal axis of the patient's spine;
the neck closure 56 is adjustable so as to accommodate a wide range of collar sizes;
the chin cup is supported by means for adjusting its height, relative to the neck support 50 so as to accommodate a wide range of neck heights;
the chin cup is supported by two adjustable lateral supports 111 so as to regulate forward and rearward chin movement with respect to the head support 20.

The device's adjustability allows one to snugly restrain the patient without excessive pressure at any single point. This avoids aggravation of the injuries, interference with blood flow, pain, discomfort, or other decubitus problems.

Structural cooperation between components of the device is also evidenced by the alignment of the cervical spine with the upper thoracic vertebrae, as the patient is immobilized from the top of the rib cage to the top of the head, restraining movement of the head, neck, and shoulders, and thus preventing aggravation of pre-existing injuries.

The foregoing description is for purposes of illustration only and is not intended to limit the scope of protection accorded this invention. The present invention may be presented in other specific embodiments without departing from the essential attributes of the present invention. It is apparent that many modifications, substitutions, and additions may be made to the preferred embodiment while remaining within the scope of the appended claims, which should be interpreted as broadly as possible.

The embodiment of the invention in which an exclusive property or privilege is claimed is defined as follows:

1. A device to immobilize the head, neck and upper torso of a patient, the device comprising:
   a) a first substrate for adapted to support the back of the patient's head;
   b) a second substrate in communication with the first substrate, whereby the second substrate is adapted to encircle the patient's neck and wherein the second substrate defines an aperture with a reversible closure adapted to receive a tracheal tube imbedded in the patient without contacting the tracheal tube; and
   c) a third substrate in communication with the second substrate, whereby the third substrate is adapted to contact the patient's chest.

2. The device as recited in claim 1 wherein the first substrate defines an aperture to facilitate access to the patient's cervical spine area.

3. The device as recited in claim 1 wherein the first substrate, the second substrate and the third substrate are integrally molded to each other.

4. The device as recited in claim 1 wherein the first substrate, the second substrate and the third substrate are transparent.

5. The device as recited in claim 1 further comprising an arcuate-shaped substrate in pivotal communication with said second substrate whereby the arcuate-shaped substrate is adapted to receive the patient's chin.

6. The device as recited in claim 5 wherein said arcuate substrate defines a distance with respect to the first substrate and wherein the device further comprises means to adjust said distance.

7. The device as recited in claim 1 wherein said first substrate allows visual inspection of the patient's ears.

8. The device as recited in claim 1 wherein said third substrate is adapted to extend at least as low as the patient's second rib.

9. The device as recited in claim 1 wherein at least one substrate comprises cushioning materials.

10. The device as recited in claim 1 wherein at least one substrate comprises one or more tubes.

11. The device as recited in claim 5 wherein said arcuate substrate defines an angle with respect to the second substrate and wherein the device further comprises means to adjust said angle.

12. The device as recited in claim 1 further comprising one or more means for removably securing the device to a backboard.

13. The device as recited in claim 12 wherein the securing means comprises an elongated substrate having a first end attached to the first substrate of the device and a second end adapted to be removably fastened to the backboard.

14. A device for simultaneously immobilizing a person's skull, cervical vertebrae, and mandible, the device comprising:

a) a first substrate which is adapted to extend from an occipital region of the skull to the first thoracic vertebrae of the person;
b) a second substrate communicating with the first substrate and extending in a direction anterior to the person, whereby the second substrate is adapted to encircle the neck of the person and wherein the second substrate defines an aperture having a removable continuous periphery; and
c) a means for immobilizing the first and second substrates to a backboard.

* * * * *

UNITED STATES PATENT AND TRADEMARK OFFICE
CERTIFICATE OF CORRECTION

| | | |
|---|---|---|
| PATENT NO. | : 7,878,995 B2 | Page 1 of 1 |
| APPLICATION NO. | : 10/633450 | |
| DATED | : February 1, 2011 | |
| INVENTOR(S) | : Robert D. Harty | |

It is certified that error appears in the above-identified patent and that said Letters Patent is hereby corrected as shown below:

In the issued patent please note the following corrections:

On page 13, column 4, line 17, delete the repeated word "surface" following "FIG. 4 is a planar view of the internal surface".

Signed and Sealed this

Nineteenth Day of April, 2011

David J. Kappos
*Director of the United States Patent and Trademark Office*